United States Patent
Racz et al.

[11] Patent Number: 5,562,722
[45] Date of Patent: Oct. 8, 1996

[54] MULTIPLE ELECTRODE CATHETER

[75] Inventors: Gabor Racz, Lubbock, Tex.; Donald R. Henderson, Johnstown, N.Y.

[73] Assignee: Medical Evaluation Devices & Instruments Corp., Gloversville, N.Y.

[21] Appl. No.: 212,545

[22] Filed: Mar. 14, 1994

[51] Int. Cl.$^6$ ........................................................ A61N 1/05
[52] U.S. Cl. ........................................................ 607/117
[58] Field of Search ........................... 607/116–117, 122, 607/126

[56] References Cited

U.S. PATENT DOCUMENTS

| | | | |
|---|---|---|---|
| 3,416,533 | 12/1968 | Fisher et al. | 607/122 |
| 3,724,467 | 4/1973 | Avery et al. | 607/117 |
| 3,757,768 | 9/1973 | Kline | 128/2 |
| 3,841,308 | 10/1974 | Tate | 128/2 |
| 4,044,765 | 8/1977 | Kline | 128/214.4 |
| 4,317,445 | 3/1982 | Robinson | 128/214.4 |
| 4,379,462 | 4/1983 | Borkan et al. | 128/786 |
| 4,525,157 | 6/1985 | Vaillancourt | 604/52 |
| 4,710,173 | 12/1987 | McFarlane | 604/168 |
| 4,721,117 | 1/1988 | Mar et al. | 128/772 |
| 4,920,980 | 5/1990 | Jackowski | 128/786 |
| 4,955,862 | 9/1990 | Sepetka | 604/164 |
| 5,098,395 | 3/1992 | Fields | 604/168 |
| 5,119,832 | 6/1992 | Xavier | 128/786 |
| 5,125,896 | 6/1992 | Hojeibane | 604/95 |
| 5,135,503 | 8/1992 | Abrams | 604/164 |
| 5,152,298 | 10/1992 | Kreyenhagen et al. | 607/116 |

FOREIGN PATENT DOCUMENTS 2481931  9/1979  France .

*Primary Examiner*—William E. Kamm
*Attorney, Agent, or Firm*—Pennie & Edmonds

[57] ABSTRACT

An electrical stimulation catheter system particularly suited for treating the epidural space of a patient, which includes a multiple electrode stimulation catheter, a stiffening element for the catheter and a device for securing an implanted catheter to the patent. A catheter according to the invention includes first and second flexible electrodes defined respectively by a portion of the catheter body and second flexible element. Preferably, leads for each electrode are secured to slideable rings around the proximal end of the catheter to prevent entanglement and confusion of the leads. A catheter securing device according to the invention includes a resilient member having a bore within which the catheter is secured. Holes for suturing or adhesive coating are provided to secure the device, which also may serve as an external electrode, to the patient.

10 Claims, 8 Drawing Sheets

MULTIPLE ELECTRODE CATHETER

BACKGROUND OF THE INVENTION

The present invention generally relates to electrical stimulation catheters typically utilized in treating the epidural space of a patient, in particular, a system for such treatment. More specifically, the invention relates to a catheter with flexible electrodes for providing electrical stimulation to the epidural space. The invention also relates to a device for securing-to-a patient a portion of an implanted epidural catheter and to a kit containing catheters and securing devices.

The application of electrical stimulation to the epidural space has proven to be effective in treating spinal pain. Single electrode spring wound catheters have been used with externally placed second electrodes. Multiple electrode catheters have also been used to provide electrical stimulation to the epidural space. The catheters are inserted into the epidural spaces through a hollow needle placed therein. Stimulation is provided by a power source that created a voltage differential across two electrodes which are electrically insulated from each other and positioned along the length of the catheter. Each of the two electrodes contact tissue or fluid in the epidural space of the patient to close an "electrical circuit". A liquid pain relieving agent, such as an anesthetic or narcotic may be injected through the catheter into the epidural space to provide further pain relief.

One spring wound catheter which has been successfully used for epidural stimulation is marketed under the tradename RACZ™ by Medical Evaluation Devices & Instruments Corporation of Gloversville, N.Y. However, this catheter has the drawback of requiring a second, external electrode. The construction of spring wound catheters in general is known from, for example, U.S. Pat. No. 3,757,768 to Kline, which discloses a spring guide catheter for intravenous feeding. The '768 catheter is composed of a helical spring covered with an inert halogenated hydrocarbon.

Prior art multiple electrode epidural catheters, such as those disclosed in U.S. Pat. No. 4,379,462 to Borkan and in U.S. Pat. No. 5,119,832 to Xavier have been constructed with rigid electrodes which hinder the process of feeding the catheter toward the epidural space. The Borkan '462 patent discloses a multi-electrode catheter which provides electrical stimulation to the spinal cord of a patient. In a preferred embodiment the '462 patent discloses electrodes which are composed of a rigid material, namely platinum rings. The Xavier '832 patent discloses a method for pain treatment which provides pulsing of electricity to the epidural space via a catheter with ring electrodes located on the external surface of the catheter. The '832 patent discloses as a preferred embodiment electrodes which are composed of rigid material, namely silver, gold or platinum. The method of the '832 patent also discloses delivery of a liquid pain relieving agent to the epidural space through the catheter.

Rigid electrodes are undesirable because, in general, they make the overall device less flexible and may become wedged in the sharp bends of the intricate passages through which a catheter must be fed. Prior art rigid electrodes may also present difficulties in fixation to the catheter. Glued connections can be unreliable and present quality control problems. Crimped connections tend to create sharp or rough spots on the electrodes that may catch on tissue or the insertion needle.

A further disadvantage of prior art stimulation or epidural catheters is the lack of early warning means to detect the presence of body fluids in the catheter lumen. For example, as the practitioner feeds the catheter toward the treatment site, the distal tip of the catheter may rupture a blood vessel. Prior art stimulation catheters such as those disclosed above, do not provide indication that a vessel has been ruptured until blood from the ruptured vessel has exited the proximal orifice of the catheter. As a result of the time required for blood to pass through the length of the catheter, the practitioner is not provided with a prompt indication of such a rupture.

Early warning means, often referred to as flashback devices, have been provided in specific configurations for other specific applications. For example, U.S. Pat. Nos. 4,710,173 to McFarlane and 4,317,445 to Robinson each disclose a flashback device which is a component of an intravenous catheter. The McFarlane '173 patent discloses a catheter insertion device in which a hollow needle is positioned within the lumen of the catheter, such that the distal end of the needle extends beyond the distal end of the catheter. When the needle penetrates a patient's vein, blood from the vein flows proximally within the needle to a portion of the device where a practitioner can observe the blood. This provides an indication that the needle is properly positioned within the patients vein. The Robinson '445 patent is essentially the same as the McFarlane '173 patent. However, the '445 invention indicates not only when the needle has entered the patient's vein, but also indicates when the cannula (catheter) has entered the patient's vein. A dead space annulus between the exterior of the needle and the interior of the cannula receives blood when the cannula has entered a vein. This blood flows proximally within the dead space annulus of the cannula to a portion of the device where a practitioner can observe the blood, thereby indicating that the cannula is properly positioned within the patient's vein.

Once an epidural catheter has been implanted in a patient and positioned to provide optimal treatment, it is desirable to leave the catheter implanted such that it does not need to be reinserted for future treatments. Allowing the catheter to remain implanted in the patient creates a risk that the catheter may be inadvertently dislodged from the position of optimal treatment or completely dislodged from the patient. Again, the prior art has failed to provide suitable means for easily securing a long term stimulation catheter and preventing it from becoming dislodged from the epidural space or completely dislodged from the patient.

SUMMARY OF THE INVENTION

Thus, it is an object of the invention to provide an epidural catheter system which includes a flexible electrode catheter for electrical stimulation of the epidural space. An epidural catheter with flexible electrodes has the advantage of facilitating insertion of the catheter since flexible electrodes readily conform to the tortuous passages which the catheter must be fed through.

This and other objects are achieved by an epidural catheter comprising a first flexible spring; a first electrical insulator covering substantially the length of the first flexible spring; a first flexible electrode defined by a distal portion of the first flexible spring which extends beyond the first electrical insulator; a second flexible spring which covers a portion of the first electrical insulator; a second electrical insulator which covers a portion of the second flexible-spring and-substantially the length of the first electrical insulator; a second flexible electrode defined by a distal portion of the second flexible spring which extends beyond the second electrical insulator; and first and second electrically conducting wires which interconnect the first and second flexible electrodes with the electrical stimulation power source.

A further object of the invention is to provide an epidural catheter as above in which a practitioner may observe the contents of the catheter lumen. Such an epidural catheter has the advantage of providing the practitioner with prompt indication that the distal tip of the catheter has ruptured a blood vessel.

It is also an object of the invention to provide an epidural catheter system which includes a device which affixes to a patient the proximal portion of an implanted epidural catheter. Affixing the protruding proximal portion of an epidural catheter reduces the risk that an implanted catheter will be inadvertently dislodged from a position of optimal treatment or completely dislodged from the patient.

This object is achieved by an epidural catheter securing member comprising a base portion; means for securing the base portion to the patient; means for defining a bore which secures the catheter; means for locking the catheter within the bore. In a preferred embodiment, the bore defining means comprises a pair of upstanding members which are adjacent to each other, with a bore defined between them. The locking means comprises the upstanding members being biased together and separable by elastically deforming the base portion. In a preferred embodiment, the base securing means includes a plurality of holes for receiving suture threads.

BRIEF DESCRIPTION OF THE DRAWINGS

The features and advantages of the invention will be more readily apparent from following the detailed description of the preferred embodiments illustrated in the drawing figures, wherein.

DETAILED DESCRIPTION OF THE PREFERRED EMBODIMENTS

Figure 1:
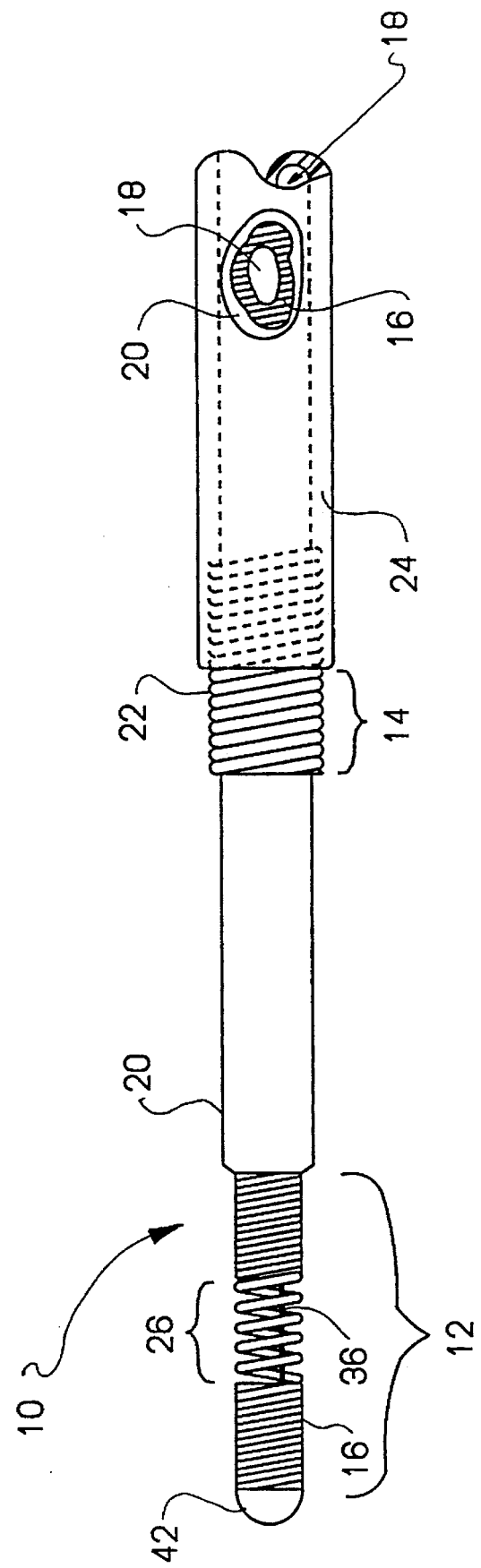
FIG. 1 is a partial sectional view of the distal end of a catheter, according to the present invention, with two flexible electrodes.

The distal end of a catheter 10 according to the present invention, with flexible electrode portions 12, 14, is illustrated in FIG. 1. Helically wound spring 16 defines inner lumen 18 and extends substantially the length of catheter 10. An electrical insulator 20 covers substantially the length of helically wound spring 16. Electrical insulator 20 is preferably Viton fluoropolymer covered with a Teflon coating, although other suitable materials may be used. Helically wound wire 22 covers a portion of electrical insulator 20. An electrical insulator 24 covers a portion of wire 22 and substantially the length of catheter 10, thereby securing wire 22 against movement on insulator 20. Electrical insulator 24 is preferably a polyester shrink tubing, although, again, other suitable materials will be apparent to persons skilled in the art.

The portions of helically wound springs 16 and wire 22 which extend beyond electrical insulators 20, 24 define flexible electrodes 12, 14 of the catheter. By forming both electrode portions 12 and 14 as part of a helically would spring or wire, they are easily flexed without significantly increasing the overall stiffness of the catheter. Spring 16 and wire 22 are electrically conductive materials, preferably ASTM 302/304 stainless steel. In a preferred embodiment spring 16 is made from a 0.005 inch wire round wound to 0.032 inch O.D. and wire 22 from a 0.003 inch×0.010 inch wire.

The flexible electrodes of the present invention facilitate insertion of the catheter, since flexible electrodes readily conform to the tortuous passages through which the catheter must be fed. Unlike the electrodes of prior art catheters which are difficult to affix to the catheter, one electrode of the present invention is inherent in the catheter and the second is easily wound around one part and secured under another part of the outer coating. In alternative embodiments, second electrode portion 14 may be formed with a flexible, electrically conductive coating applied in a liquid form. It is also contemplated that a flexible electrically conductive tubing may be secured around insulator 20 in the same manner as wire 22.

Fluids may readily communicate between the lumen be of the catheter 10 and the epidural space or blood vessels of the patient through spread portion 26. Spread portion 26 comprises a portion of helically wound spring 16 in which each coil is separated from the coil immediately distal and the coil immediately proximal. Spread portion 26 can be used to introduce, e.g., pain relieving agent at the treatment site or to aspirate during a procedure. The proximal orifice of the catheter communicates with spread portion 26 through catheter inner lumen 18, defined by spring 16. In addition, blood from a ruptured vessel may enter through spread portion 26 and flow into lumen 18.

Figure 2:
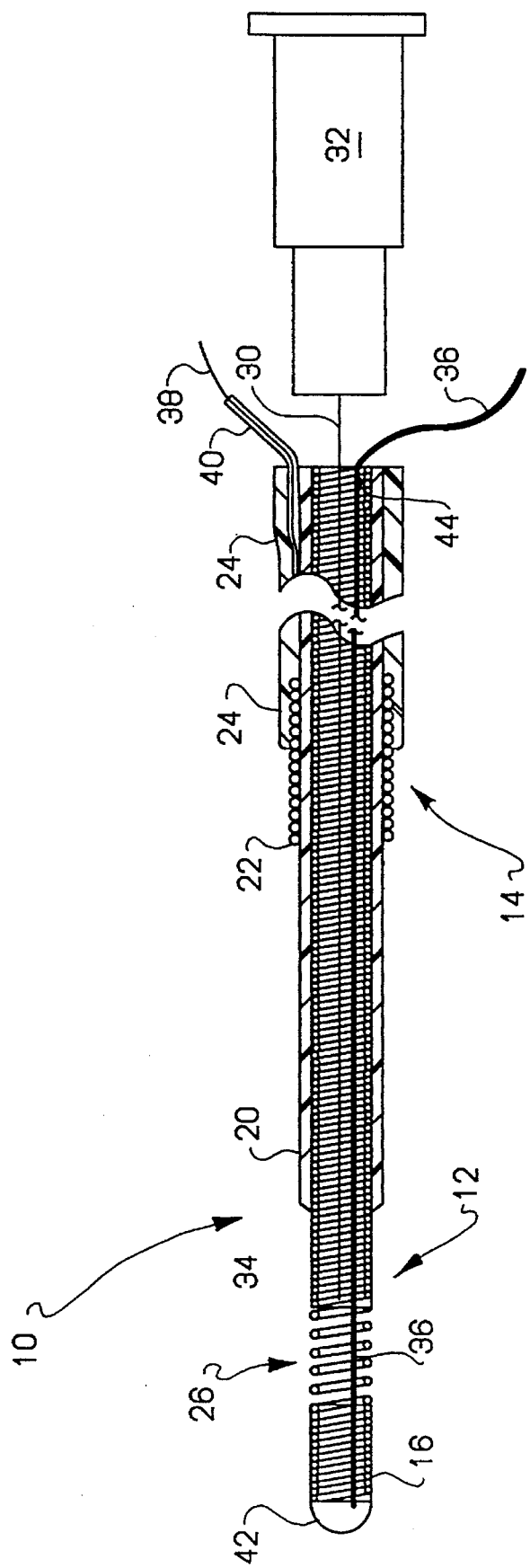
FIG. 2 is a partial sectional view of the catheter of FIG. 1, illustrating further features of the invention.

Referring to FIG. 2, further features of the invention are described. Stylet 30 fits within the lumen 18 of the catheter. Insertion/retrieval knob 32 is attached to the proximal end of stylet 30. Stylet 30 facilitates insertion of catheter 10 into the epidural space by stiffening the majority of the length of the catheter to increase pushability. When fully inserted into the catheter, distal tip 34 of stylet 30 is positioned just before spread portion 26. This maintains the distal end of the catheter as highly flexible and prevents tip 34 of the stylet from passing between the spread helices 26 to damage surrounding tissue when sharp bends are traversed. The stylet is preferably of ASTM 302/304 stainless steel.

Electrically-conducting-wires or ribbons 36, 38 interconnect flexible electrodes 12, 14, respectively, with an electrical stimulation power source. Electrically conducting wires 36, 38 are preferably 0.003 inch×0.010 inch ASTM 302/304 stainless steel wire or ribbon. Electrical insulator 40 is preferably polyester shrink tubing and covers the proximal end of wire 38, a short distance under insulator 24. Electrical insulator 40 ensures that electrically conducting wire 34 is insulated from electrically conducting wire 36 outside the catheter. These wires or ribbons may be further insulated with a Teflon or similar materials.

In order to provide a smooth, rounded distal tip, distal ball 42 is formed by melting the distal end of spring 16. Wire 36 also serves as a safety ribbon to prevent separation of the distal ball and extension of spring body 16. Wire 36 is therefore welded to ball 42 and also tack welded to spring 16 at the proximal weld 44.

Figure 3:
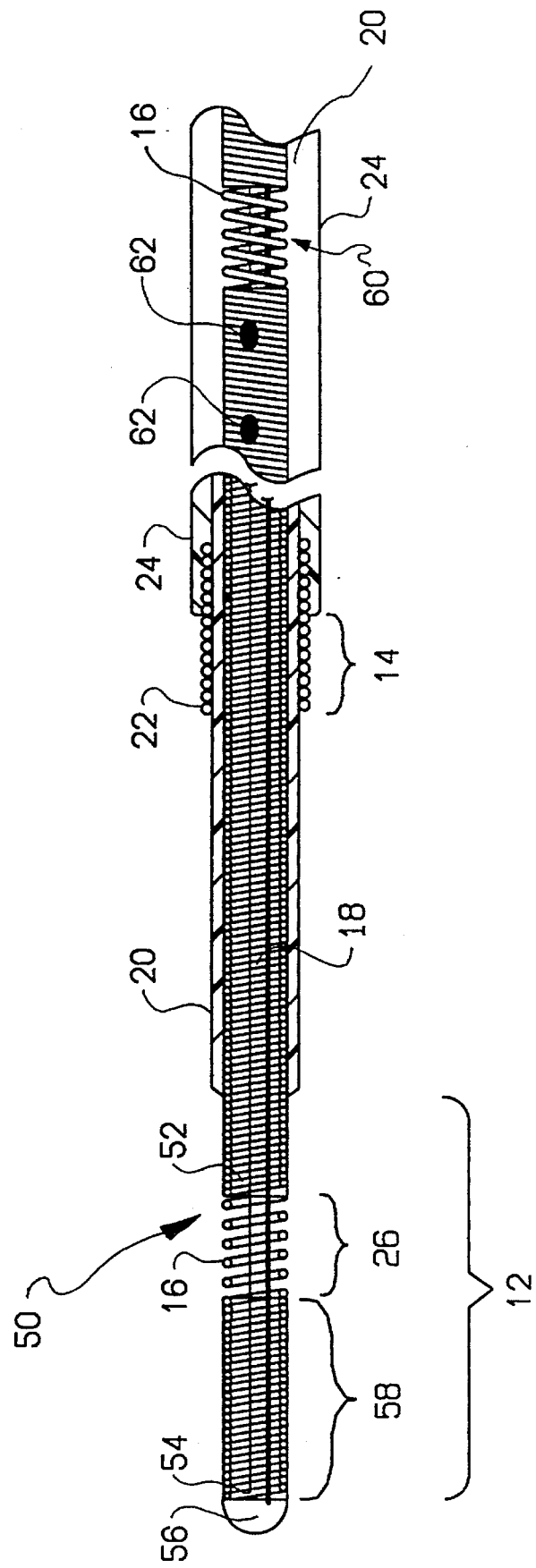
FIG. 3 is a partial sectional view similar to FIG. 2, showing an alternative embodiment of the catheter according to the invention having an extended distal end.

FIG. 3 illustrates an alternative embodiment which allows the practitioner to safely vary the stiffness of the distal end of catheter 50 as it is advanced or manipulated. Stiffness is increased by moving stylet 52 distally within the lumen 18 such that the distal tip 54 of stylet 52 approaches the distal tip 56 of catheter 50. Stiffness is reduced by moving stylet 52 proximally within lumen 18, such that stylet distal tip 56 retreats from the distal tip 56 of catheter 50. A stiff distal end is required when, for example, the catheter must enter a constricted orifice or penetrate passages occluded by scar tissue. A stiff distal end is required in these situations since an axial force will be applied at the distal tip of the catheter by the constricted orifice or scar tissue as the practitioner feeds the catheter forward. The stiff distal end ensures that the distal tip of the catheter will be able to penetrate such a constricted orifice or scar tissue without buckling of the distal end. A distal end with reduced stiffness is desired when the distal end must be fed through a tortuous passage, since a flexible distal end will conform to the shape of such a passage. In particular, the stylet may be withdrawn to be behind the spread portion as the catheter is inserted to provide an extremely flexible tip and prevent damage to the dura during insertion.

In order to allow stylet 52 to be safely manipulated as described above, catheter 50 is provided with an extended distal portion 58. Distal portion 58 of catheter 50 is preferably at least about twice as long as the portion of spring 16 that is distal to spread 26 of catheter 10 shown in FIGS. 1 and 2. Thus, there is little danger that distal tip 54 of stylet 52 will pass between spread 26 and damaging surrounding tissue. If desired, a ball may be welded at the end of the stylet to further ensure that the tip will not pass through the catheter wall. In an example embodiment, spread portion 26, and the immediately proximal section of spring 16 are each approximately 3/16 inch in length, whereas extended distal portion 58 is 3/8 inch.

A further feature of the present invention illustrated in FIG. 3 is observation window or viewing portion 60. The contents of lumen 18 can be readily observed through window portions 60 wherein each coil of helically wound spring 26 is separated from its distal and proximal adjacent coils in the same manner as for spread portion 26. Insulating covers 20 and 24 are transparent to allow observation of the contents of lumen 18. Transparent cover material is preferably a fluoroethyl polymer heat shrink tubing; however, persons skilled in the art may select other suitable coverings. Unlike prior art stimulation catheters, which do not provide indication that a blood vessel has been ruptured until blood exits the proximal orifice of the catheter, window portion 60 provide prompt indication that a blood vessel has been ruptured.

Multiple markings 62 are equally spaced along the length of the catheter to serve as a measuring device which provides the practitioner with a convenient indication of the depth to which the catheter has been inserted into the patient's body. Preferably, the markings begin about 15 cm proximal of the distal end of insulator 20 and are spaced about 1 cm apart. Such markings may be used on other embodiments disclosed herein.

Figure 4:
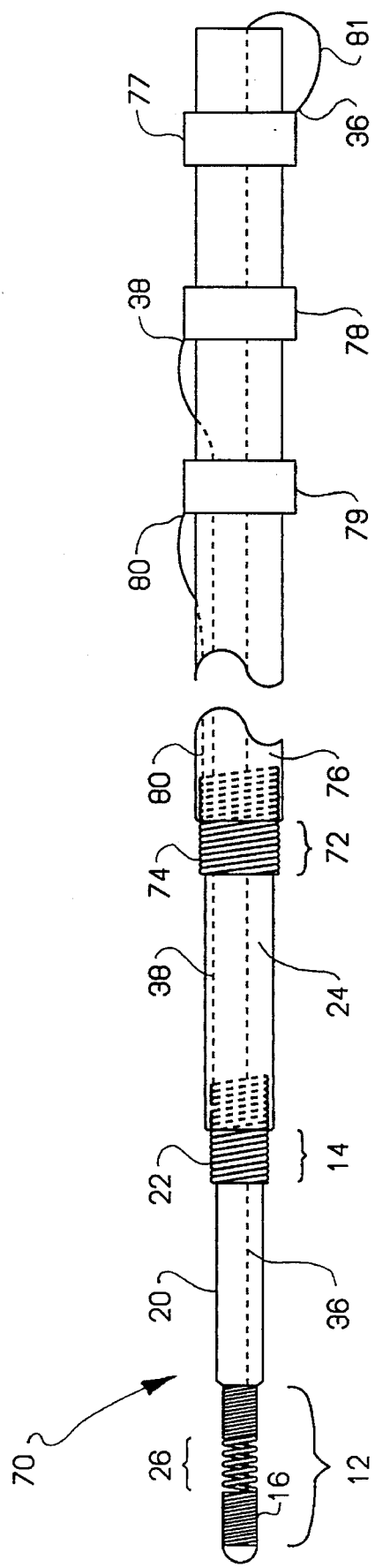
FIG. 4 is a side view of the distal end of a further alternative embodiment according to the present invention.

A further alternative embodiment of the invention having multiple electrodes is shown in FIG. 4. Catheter 70 has a third flexible electrode portion 72. Electrode 72 is added to the catheter in essentially the same way as electrode portion 14, described above. Helically wound spring 74 covers a portion of electrical insulator 24. Helically wound spring 74 is also an electrically conductive material, preferably ASTM 302/304 stainless steel ribbon. An electrical insulator 76 covers a portion of helically wound spring 74 extends proximally over the length of catheter 70. Electrical insulator 76 is preferably a polyester or FEP shrink tubing. The portion of helically wound spring 74, which extends beyond electrical insulator 76 defines additional flexible electrode portion 72 of catheter 70. Electrically conducting wire or ribbon 80 interconnects the additional flexible electrode 72 with the electrical stimulation power source. Electrically conducting wire or ribbon 80 is also preferably of ASTM 302/304 stainless steel.

The proximal ends of electrically conducting ribbons 36, 38 and 80 can extend out of the proximal end of the catheter, where they will be partially covered with a shrink wrap tubing to prevent short circuit as shown at 40 in FIG. 2. However, in a preferred embodiment of the present invention, ribbons 36, 38 and 80 are secured to conductive rings 77, 78 and 79, respectively, at the proximal end. The rings and ribbons may be secured by tack welding or other electrically conductive means. Preferably, the ribbon runs under the ring and is secured to the ring on the side opposite from where it exits the catheter.

Rings 77–79 are made from a conductive material such as ASTM 302/304 stainless steel and are preferably about 0.003 inches thick and about 0.030 inches wide. Although preferred, a conductive material is not required. The rings have an internal diameter slightly larger than the outside diameter of the catheter to allow them to slide along the catheter's length. The outside diameter of the rings is sized to allow the rings to easily pass through the insertion needle of choice so that the insertion needle can be removed after the catheter is in place. By sliding a ring along the catheter, the attached ribbon separates from the catheter to form a loop, as shown at eL in ribbon 36. This allows a clip, such as an alligator or no-slip clip (not shown), to be easily affixed to the ribbon for connection to the stimulation source. Alternatively, the clip may be affixed to the electrically conductive ring. The ring arrangement described above provides a number of advantages, such as eliminating dangling wires, facilitating the determination of which ribbon lead goes to which electrode and also providing two secure contact points for each electrode.

Persons of ordinary skill in the art will appreciate that any number of multiple flexible electrodes and corresponding rings may be added in the manner described above. Such additional electrodes allow the practitioner to provide electrical stimulation to the epidural space of a patient across a variety of combinations of electrodes, to determine and provide the optimal treatment for a particular patient. Rings such as 77–79 also may be employed with the bi-polar catheter shown in FIG. 2 or with any other number of electrodes.

Figure 5:
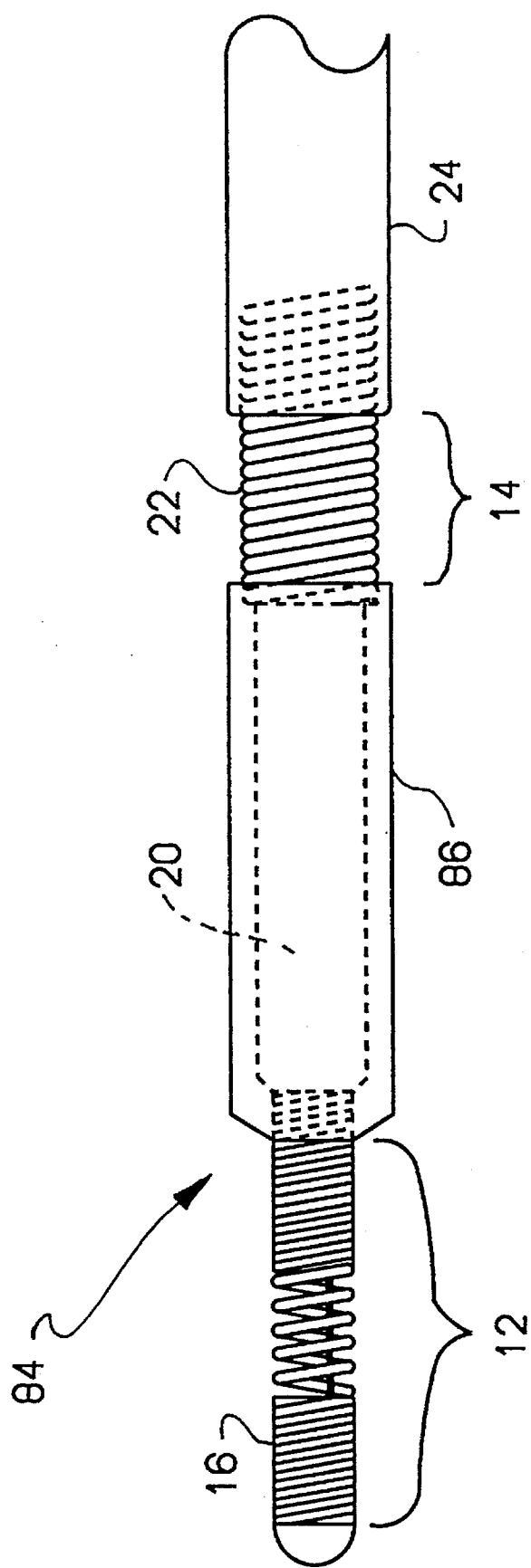
FIG. 5 is a side view of the distal end of a catheter according to another embodiment of the invention, similar to of FIG. I with a securing member at the distal end of the second electrode.

Catheter 84 illustrated in FIG. 5 includes a securing member 86 which covers portions of electrical insulator 20 and electrodes 12 and 14. Securing member 86 ensures that helically wound wire 22 will not be stretched distally along the length of electrical insulator 20. Securing member 86 is preferably of a polyester shrink tubing.

Figure 6:
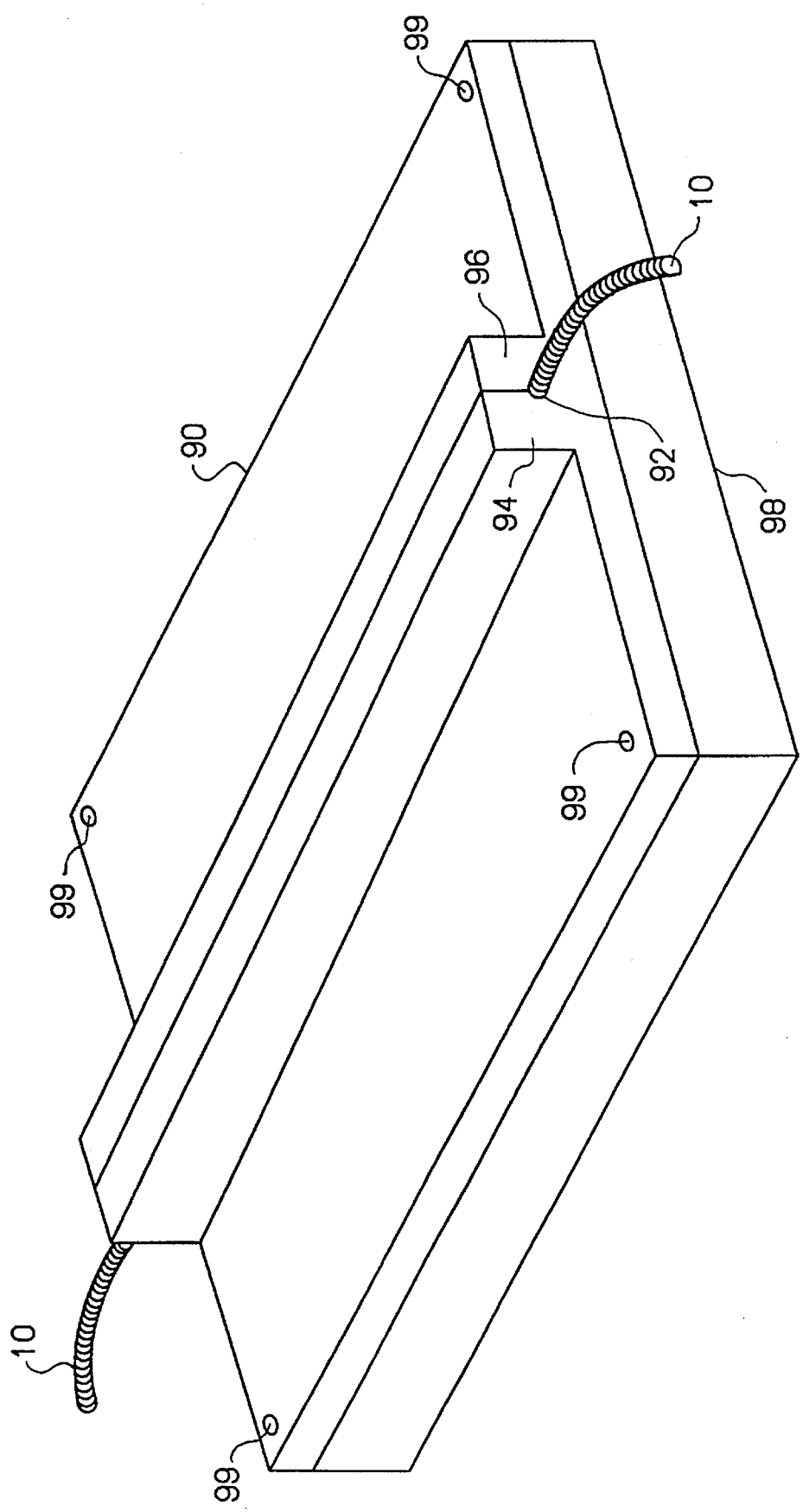
FIG. 6 is a perspective view of a securing device of the invention.
Figure 7:
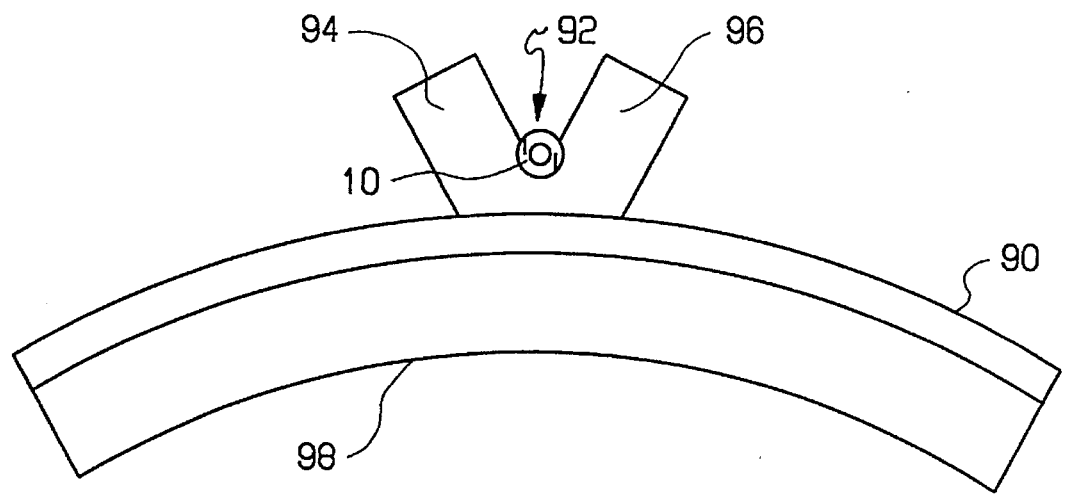
FIG. 7 is a view through line 1—1 of FIG. 7, in which the device is deformed to receive a catheter.

A further component of the system according to the present invention is a device for securing an epidural catheter to the body of a patient as illustrated in FIG. 6. Securing device 90 is provided with a longitudinal bore 92 for receiving catheter, e.g. catheter 10. Preferably bore 92 has an inside diameter slightly smaller than the catheter outside diameter so that the material of device 90 is compressed slightly when gripping the catheter. Catheter 10 is secured to device 90 by elastically deforming the device along an axis parallel to the axis of bore 92 such that bottom face 94 of the securing device is concave. FIG. 7 illustrates securing device 90 in such a deformed state. Upon such deformation, walls 94 and 96 separate into a V shape and bore 92 is exposed. A length of catheter be is placed within bore 92. The practitioner then allows device 90 to return to its predeformed state as illustrated in FIG. 6. The surface of bore 92 may be coated with an adhesive or other adhering material to further facilitate securing of the catheter. Additional securing means, such as adhesive or a tongue and groove lock, can be provided between walls 94 and 96. Device 90 is preferably a rubber material such as silicone, although other elastically deformable materials may be used. Additionally, bottom portion 97 can be made from an electrically conductive material so that it can also serve as an external electrode to supplement the catheter electrodes, or for use with a single pole catheter.

Catheter securing device 90 (and device 100 discussed below) may be affixed to the patient by an adhesive coating bottom face 98 of the device. In an Alternatively, the device may be sutured to the patient by utilizing holes 99. Utilizing catheter securing devices 90 or 100 to secure a proximal portion of a catheter which protrudes from a patient's body ensures that the catheter will not be inadvertently dislodged from a position of optimal treatment or completely dislodged from the patient.

Figure 8:
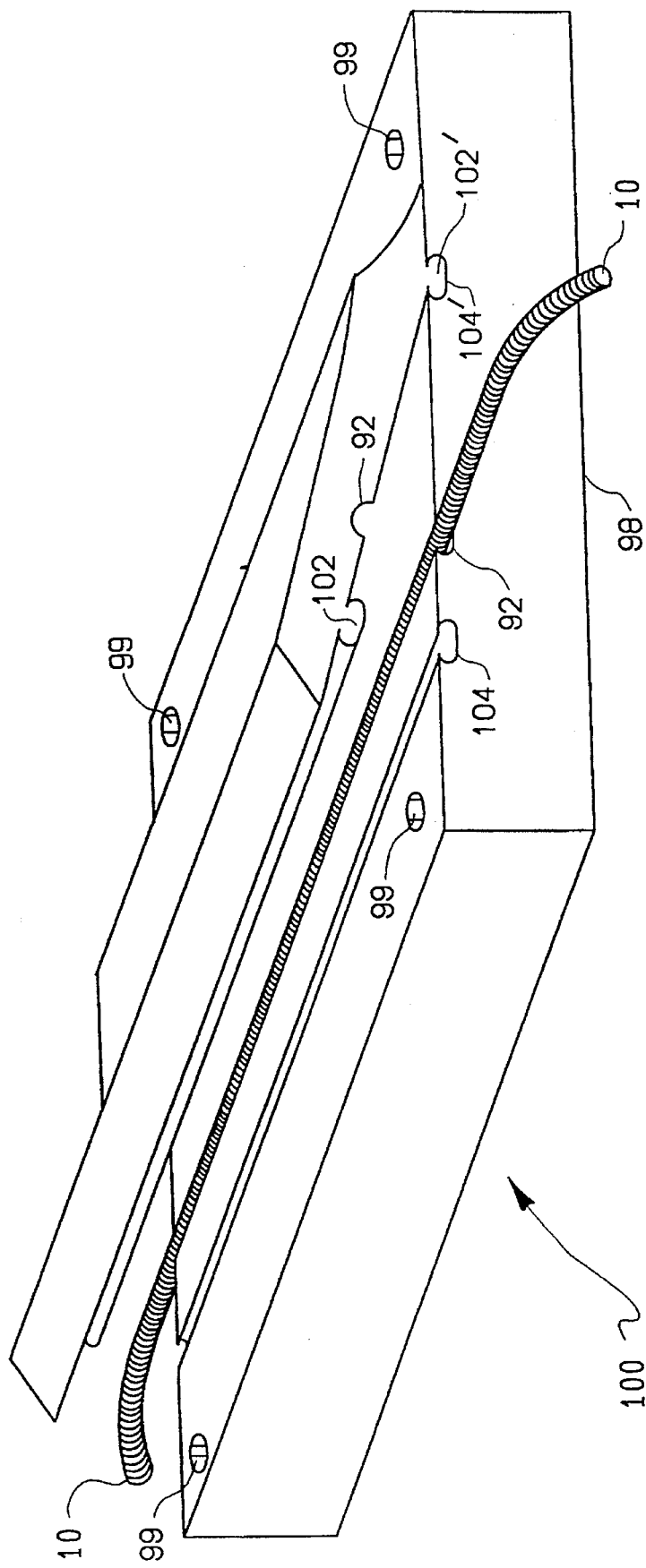
FIG. 8 is a perspective view of an alternative embodiment of the device illustrated in FIG, 7; and FIG, 9 is a top view of a kit according to the present invention.

An alternative embodiment of a device for securing an epidural catheter to the body of a patient is illustrated in FIG. 8. Catheter 10 is secured to securing device 100 by removing tongue 102 from groove be such that bore 92 is exposed. A length of catheter be is placed within bore 92. Upon securing tongue 102 within groove be4 the catheter is enclosed within bore 92. Bore 92 is sized as described above and may be coated with an adhesive to further facilitate securing of the catheter. Device 100 is also preferably a rubber such as silicone or other elastically deformable material. Device 100 can be formed as a single piece with a slit providing the opening to exposed bore 92 or, in a preferred embodiment, as shown in FIG. 8, device 100 is formed in two pieces. Tongue and groove connections 102, 102' and 104, 104' hold the two pieces together.

Figure 9:
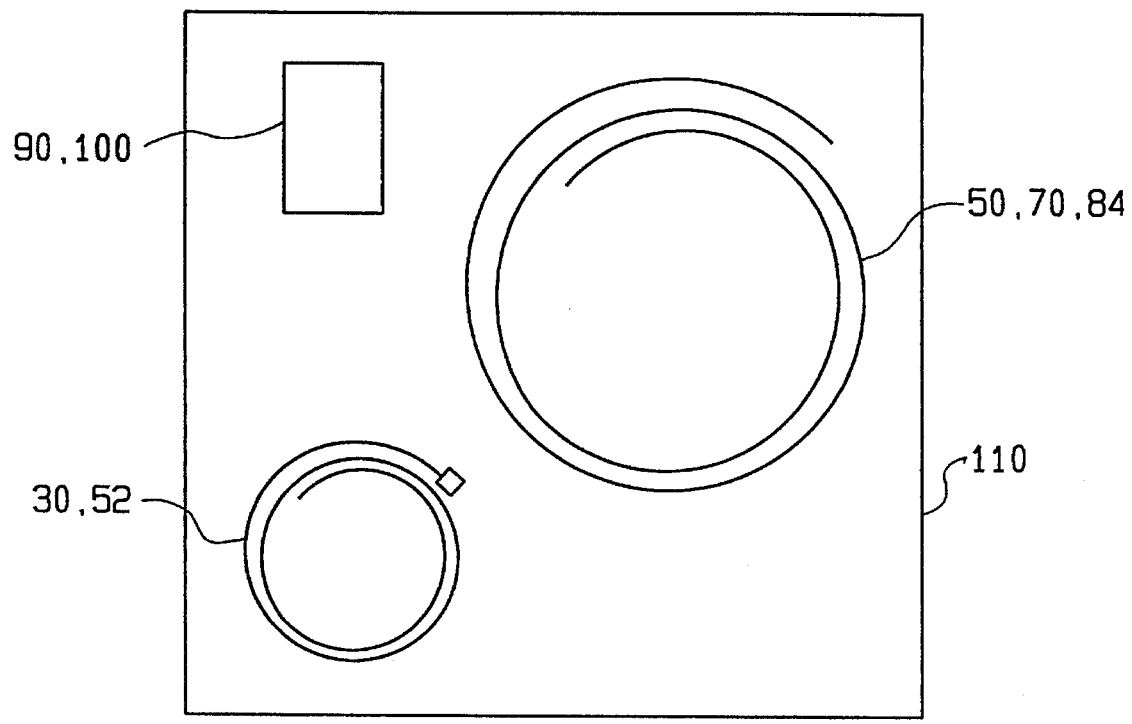

The various components of the system according to the present invention are separately described above. The components also may be provided in kit form by packaging various components together in a sterile packaging 110 as shown in FIG. 9. Components used together such as one or more catheters 50, 70, 84, appropriate stylets 30, 52 and an anchoring device 90, 100 would typically be provided together.

What is claimed is:

1. A catheter system, comprising: a helically wound multiple electrode stimulation catheter comprising, a helically wound inner member having distal and proximal ends, wherein at least the distal end is an electrically conductive material and wherein said inner member defines an inner lumen of said catheter, a first insulating layer covering less than all of said inner member, wherein the distal end of said inner member is exposed to define a first, flexible helically wound electrode, wherein said first electrode comprises a first proximal portion having closely wound helices, a second central portion having spread apart helices to define a passage for fluid communication with said lumen, and a third distal portion having closely wound helices, a second flexible electrode disposed around said first insulating layer and spaced proximally a predetermined distance from said first electrode, and a second insulating layer around said catheter beginning at the second electrode and extending to the proximal end of the inner member; and at least one stiffening element having a predetermined length and adapted to be inserted into the inner lumen of said catheter.

2. The catheter system according to claim 1, wherein the length of said at least one stiffening element is sufficient to extend from the proximal end of the inner member beyond the spread apart central portion when fully inserted into the inner lumen of the catheter.

3. The catheter system according to claim 2, wherein:

said third distal portion has a length equal to at least the length of said first and second portions together; and said at least one stiffening element has a distal tip and said element is configured and dimensioned to be variably positioned within said catheter with the distal tip variably located in said third portion.

4. The catheter system according to claim 1, wherein said catheter includes at least one viewing portion, spaced proximally from said first and second electrodes, wherein the helices of the inner member are spread apart, and said first and second insulating layers are sufficiently transparent to permit viewing of fluids within said catheter.

5. The catheter system according to claim 2, further including at least one securing member adapted to receive and secure said at least one catheter to a patient's body, wherein said securing member comprises:

a base portion, wherein the base portion includes an outer skin contacting portion comprised of a conductive material to provide an external electrode;

means for affixing said base portion to a patient;

means for defining a catheter securing bore on said base portion; and means for locking said catheter within said bore.

6. A catheter system including: at least one spring wound multiple electrode stimulation catheter, comprising, a helically wound spring of an electrically conductive material having distal and proximal ends, said spring defining an interior lumen of said catheter, a first insulating layer of an electrically insulating material having distal and proximal ends, said first layer covering a portion of said spring, wherein a first electrode is defined by an exposed distal portion of said spring which extends beyond the distal end of said first insulating layer, a first electrical conductor having distal and proximal ends, the distal end being secured and electrically connected to said first electrode at the distal end, extending through said interior lumen and being secured to the spring adjacent the proximal end, a wire of electrically conductive material helically wound around a portion of said first insulating layer, said wire being spaced proximately from the distal end of said first insulating layer, a second insulating layer of an electrically insulating material having distal and proximal ends, said second layer covering a portion of both said helically wound wire and said first insulating layer, wherein a second electrode is defined by an exposed distal portion of said wire which extends beyond the distal end of said second insulating layer, and a second electrical conductor having distal and proximal ends, the distal end being electrically connected to said second electrode, said second conductor extending between said first and second insulating layers;

at least one stiffening element having a predetermined length and adapted to be freely inserted into the lumen of said catheter; and at least one securing member adapted to receive and secure said catheter to a patient's body, comprising a base portion securable to a patient and a catheter securing means for securing said catheter to said base portion, wherein said catheter securing means comprises a pair of upstanding members disposed adjacent to each other on one side of said base portion and defining a bore between them, wherein the base is adapted to bend, thereby separating the upstanding members for receiving said catheter.

7. A spring wound multiple electrode stimulation catheter comprising:

a helically wound spring inner member, comprising a plurality of coils and having distal and proximal ends, wherein at least the distal end is an electrically conductive material and wherein said inner member defines an inner lumen of said catheter;

a first insulating layer covering less than all of said inner member, wherein the distal end of said inner member is exposed to define a first, flexible helically wound electrode and wherein said first electrode comprises a first proximal portion having closely wound helices, a second central portion having spread apart helices to define a passage for fluid communication with said lumen, and a third distal portion having closely wound helices;

a second flexible electrode, disposed around said first insulating layer and spaced proximally a predetermined distance from said first electrode; and a second insulating layer around said catheter beginning at the second electrode and extending to the proximal end of the inner member.

8. The catheter according to claim 7, further comprising:

a first electrical conductor having distal and proximal ends, the distal end being secured and electrically connected to said first electrode at the distal end, extending through said interior lumen and being secured to said helically wound spring adjacent to the proximal end; and a second electrical conductor having distal and proximal ends, the distal end being electrically connected to said second electrode, said second conductor extending between said first and second insulating layers.

9. The catheter according to claim 7, wherein said second electrode is defined by five to twenty five coils of said second spring.

10. The catheter according to claim 7, wherein the distal end of said first helically wound spring forms a spherically shaped tip.

* * * * *